United States Patent
Omary et al.

(10) Patent No.: US 7,745,402 B2
(45) Date of Patent: Jun. 29, 2010

(54) METHOD OF TREATING PANCREATITIS

(75) Inventors: Bishr Omary, Mountain View, CA (US); Stephen Collins, Lake Forest, IL (US)

(73) Assignee: Lundbeck Inc., Deerfield, IL (US)

( * ) Notice: Subject to any disclaimer, the term of this patent is extended or adjusted under 35 U.S.C. 154(b) by 0 days.

(21) Appl. No.: 11/542,522

(22) Filed: Oct. 2, 2006

(65) Prior Publication Data
US 2007/0232525 A1     Oct. 4, 2007

Related U.S. Application Data

(60) Provisional application No. 60/722,284, filed on Sep. 30, 2005.

(51) Int. Cl.
*A61K 38/00*     (2006.01)
(52) U.S. Cl. .......................................... 514/12
(58) Field of Classification Search .................... 514/12
See application file for complete search history.

(56) References Cited

U.S. PATENT DOCUMENTS 6,689,745 B1    2/2004  Itakura et al.
2004/0228930 A1 * 11/2004 Billiar et al. ................ 424/699

OTHER PUBLICATIONS

Sato et al., FEBS Letters, 1997, 405(2), 219-223.*
Rossi et at. "Inhibiton of Human lymphocyte Ferrochelatase Activity" by Hemin. Biochimica et Biophysica Acta (Netherlands), May 8, 1990, V1038(3). p. 375-81 (abstract only).
Wagener et al. "Hemin is a Potent Inducer of Inflammation in Mice and is Counteracted by Heme Oxygenase". Blood Journal. Sep. 15, 2001. vol. 98(6). p. 1802-1811, p. 1802, 1809.
International Search Report for International Application No. PCT/US06/38509.
Perez-Mateo M. "How We Predict the Etiology of Acute Pancreatitis". J. Pancreas (online) 2006 7(3) ;257-261.
Gullo M., Migliori M., Olah A., Farkas G., Levy P., Arvanitakis C, et al. "Acute Pancreatitis in Five European Countries; Etiology and Mortality". Pancreas 202; 24:223-7.

* cited by examiner

*Primary Examiner*—Maryam Monshipouri

(57) ABSTRACT

The present invention provides a method of treating pancreatitis comprising administering to a human in need thereof an effective amount of hemin. The administration of hemin is preferably parenteral. In another aspect, the present invention provides a method of pancreatitis prophylaxis comprising administering to a human in need thereof an effective amount of hemin. In a still further aspect, the present invention contemplates a method of inducing an HO gene comprising administering to a human in need thereof an HO-inducing effective amount of hemin. Preferably, the HO gene is the HO-1 gene. In a still further aspect, the present invention contemplates a method of inducing an HO gene in leukocytes for recruitment to the pancreas to treat pancreatitis comprising administering to a human in need thereof an HO-inducing effective amount of hemin. In another embodiment, the present invention contemplates a method of inducing an HO gene in leukocytes for recruitment to the pancreas for prophylaxis of pancreatitis comprising administering to a human in need thereof an HO-inducing effective amount of hemin. In a yet further aspect, the present invention provides a method of ex vivo treatment of pancreatitis comprising providing peripheral blood leukocytes, followed by contact with hemin to form induced peripheral blood leukocytes then infusing the induced peripheral blood leukocytes into a human in need thereof.

5 Claims, 12 Drawing Sheets figure 3
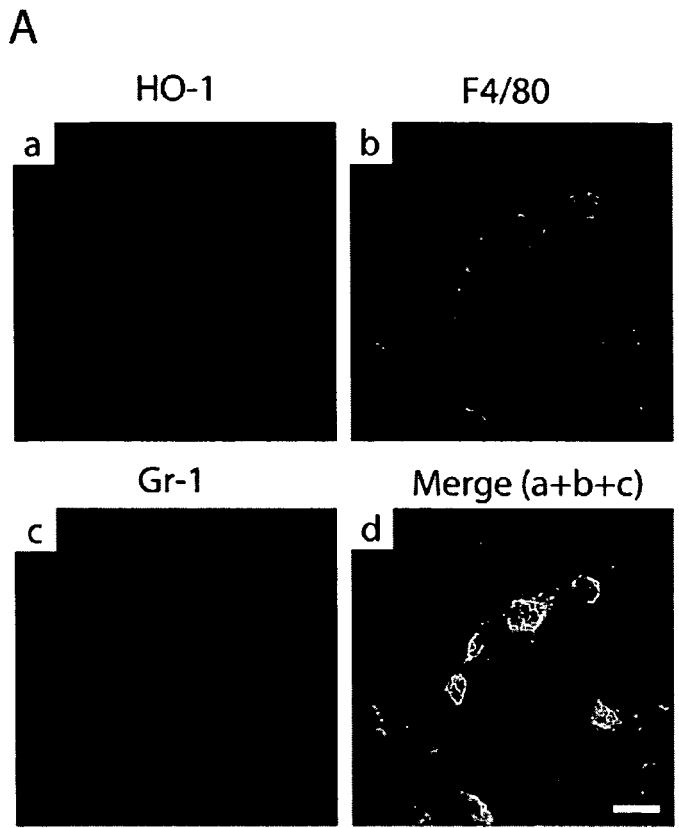
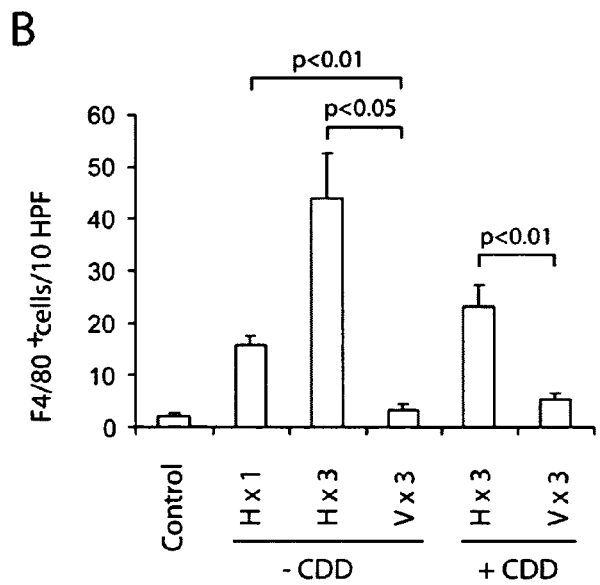
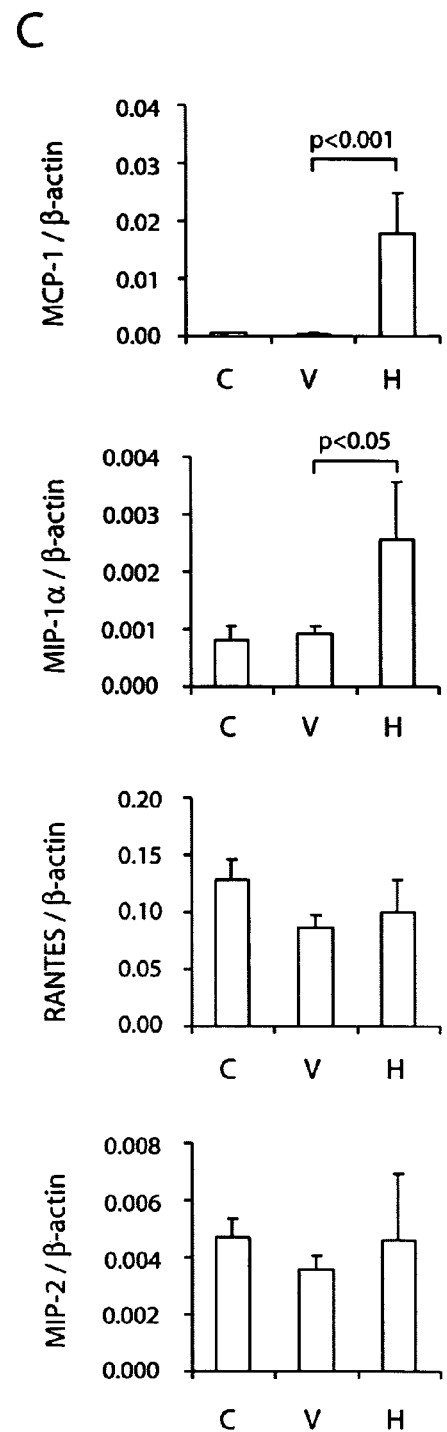

figure 5
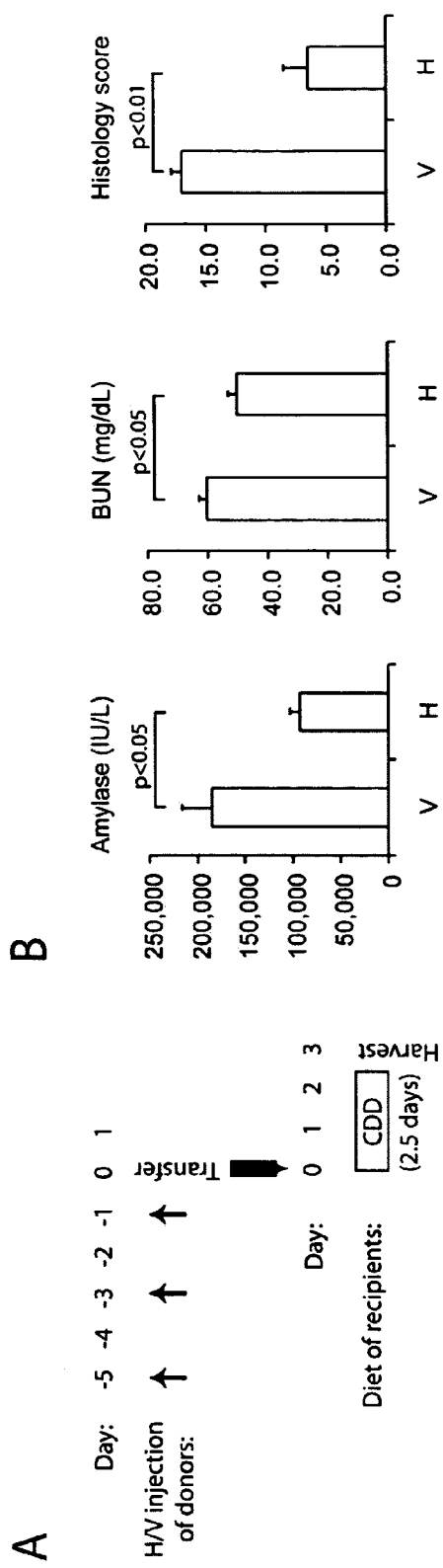
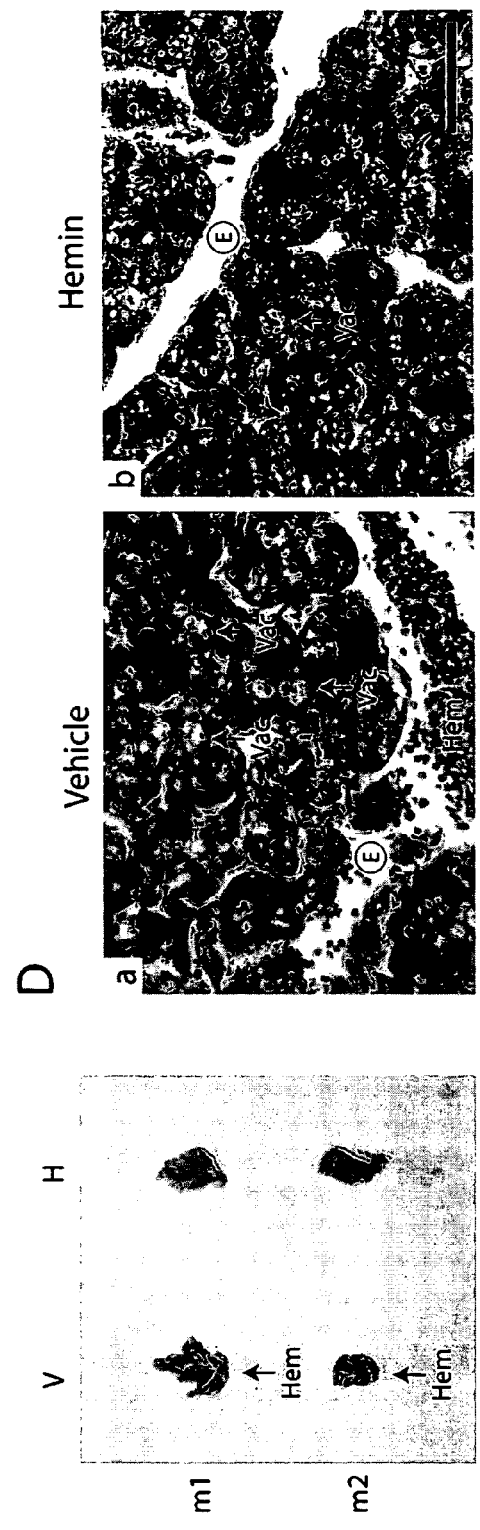

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
uggcuuccuu guaccauaut t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic -continued oligonucleotide

<400> SEQUENCE: 2
auaugguaca aggaagccat t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
gccacacagc acuauguaat t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
uuacauagug cuguguggct t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
gcgcgcuuug uaggauucgt t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
cgaauccuac aaagcgcgct t                                              21

METHOD OF TREATING PANCREATITIS

CROSS-REFERENCE TO RELATED APPLICATIONS

This application claims priority from U.S. provisional patent application 60/722,284 filed on Sep. 30, 2005.

STATEMENT REGARDING FEDERALLY SPONSORED RESEARCH

This work was supported by Department of Veterans Affairs and NIH Grant DK073909. The government may have certain rights related thereto.

BACKGROUND OF THE INVENTION

Acute pancreatitis is a severely debilitating, sometimes lethal disease in humans. Most therapies are supportive and target the hemodynamic effects such as dehydration with removal of precipitating factors that include, among others, alcohol or biliary obstructing calculi. Banks, P. A. 1997. Practice guidelines in acute pancreatitis. *Am. J. Gastroenterol.* 92:377-386; Baron, T. H., and Morgan, D. E. 1999. Acute necrotizing pancreatitis. *N. Engl. J. Med.* 340:1412-1417. There is therefore a long-felt unmet need for a novel therapy for the treatment of pancreatitis that provides more than palliative care. There is also a need for effective agents that can be used as prophylaxis towards pancreatitis in high risk patients.

Hemin up-regulates HO-1, a stress-induced enzyme implicated in protection from a variety of injuries while its related isoform HO-2 is constitutively expressed. Poss, K. D., and Tonegawa, S. 1997. Heme oxygenase 1 is required for mammalian iron reutilization. *Proc. Natl. Acad. Sci. U.S.A.* 94:10919-10924; Soares, M. P., Lin, Y., Anrather, J., Csizmadia, E., Takigami, K., Sato, K., Grey, S. T., Colvin, R. B., Choi, A. M., Poss, K. D., et al. 1998. Expression of heme oxygenase-1 can determine cardiac xenograft survival. *Nat. Med.* 4:1073-1077; Lee, T. S., and Chau, L. Y. 2002. Heme oxygenase-1 mediates the anti-inflammatory effect of interleukin-10 in mice. *Nat. Med.* 8:240-246; Otterbein, L. E., Soares, M. P., Yamashita, K., and Bach, F. H. 2003. Heme oxygenase-1:unleashing the protective properties of heme. *Trends Immunol.* 24:449-455.; Durante, W. 2003. Heme oxygenase-1 in growth control and its clinical application to vascular disease. *J. Cell. Physiol.* 195:373-382; Sikorski, E. M., Hock, T., Hill-Kapturczak, N., and Agarwal, A. 2004. The story so far: Molecular regulation of the heme oxygenase-1 gene in renal injury. *Am. J. Physiol. Renal Physiol.* 286:F425-441. Heme oxygenases catalyze the rate-limiting step in heme degradation to produce carbon monoxide (CO), iron, and biliverdin in equimolar amounts. Otterbein, L. E., et al., *Trends Immunol.* 24:449-455; Sikorski, E. M., et al., *Am. J. Physiol. Renal Physiol.* 286:F425-441; Tenhunen, R., Marver, H. S., and Schmid, R. 1968. The enzymatic conversion of heme to bilirubin by microsomal heme oxygenase. *Proc. Natl. Acad. Sci. U.S.A.* 61:748-755. Biliverdin is then reduced to bilirubin by biliverdin reductase. HO-1 (32 kDa; also referred to as heat shock protein-32) and HO-2 (36 kDa) are unique gene products that share nearly 40% identity at the amino acid level. Otterbein, L. E., et al., *Trends Immunol.* 24:449-455; Sikorski, E. M., et al., *Am. J. Physiol. Renal Physiol.* 286:F425-441. The role of HO-1 or hemin in the exocrine pancreas and their potential modulation of pancreatic injury are unknown. The only descriptions of HO-1 in the exocrine pancreas are two reports during 1997 that demonstrate HO-1 induction in caerulein-mediated mouse pancreatitis and in AR42J rat acinar cells exposed to $H_2O_2$ or $CdCl_2$. Fu, K., Sarras, M. P., Jr., De Lisle, R. C., and Andrews, G. K. 1997. Expression of oxidative stress-responsive genes and cytokine genes during caerulein-induced acute pancreatitis. *Am. J. Physiol.* 273:G696-705; Sato, H., Siow, R. C., Bartlett, S., Taketani, S., Ishii, T., Bannai, S., and Mann, G. E. 1997. Expression of stress proteins heme oxygenase-1 and -2 in acute pancreatitis and pancreatic islet betaTC3 and acinar AR42J cells. *FEBS Lett.* 405:219-223, HO-1 null mice develop anemia and high tissue iron levels with consequent oxidative damage in the liver, glomerulonephritis and splenomegaly. These mice have >80% embryolethality and most surviving mice die within 6 months due to presumed multi-organ failure. Poss, K. D., and Tonegawa, S., *Proc. Natl. Acad. Sci. U.S.A.* 94:10919-10924; Soares, M. P., et al., *Nat. Med.* 4:1073-1077; Yet, S. F., Perrella, M. A., Layne, M. D., Hsieh, C. M., Maemura, K., Kobzik, L., Wiesel, P., Christou, H., Kourembanas, S., and Lee, M. E. 1999. Hypoxia induces severe right ventricular dilatation and infarction in heme oxygenase-1 null mice. *J. Clin. Invest.* 103:R23-29. There is also a single reported case of HO-1 deficiency identified in a child who died at the age of 6 with renal disease and intracranial hemorrhage. Yachie, A., Niida, Y., Wada, T., Igarashi, N., Kaneda, H., Toma, T., Ohta, K., Kasahara, Y., and Koizumi, S. 1999. Oxidative stress causes enhanced endothelial cell injury in human heme oxygenase-1 deficiency. *J. Clin. Invest.* 103:129-135; Kawashima, A., Oda, Y., Yachie, A., Koizumi, S., and Nakanishi, I. 2002. Heme oxygenase-1 deficiency: the first autopsy case. *Hum. Pathol.* 33:125-30. The effect HO-1 absence in humans or mice on pancreatic pathology is unknown.

Hemin is the prosthetic moiety for a broad range of proteins that play essential roles in oxygen delivery, mitochondrial function, and signal transduction including hemoglobin, cytochromes, prostaglandin endoperoxide and nitrous oxide synthases, catalase and peroxidases. Various formulations of hemin such as hematin and other alternate intravenous formulations (e.g. panhematin) are currently available and have been used in patients since the 1970's with reported minimal side effects to successfully treat acute porphyrias, to control liver allograft failure due to recurrence of erythropoietic protoporphyria, and in patients with thalassemia intermedia. Tenhunen, R., and Mustajoki, P. 1998. Acute porphyria: treatment with heme. *Semin. LiverDis.* 18:53-55; Dellon, E. S., Szczepiorkowski, Z. M., Dzik, W. H., Graeme-Cook, F., Ades, A., Bloomer, J. R., Cosimi, A. B., and Chung, R. T. 2002. Treatment of recurrent allograft dysfunction with intravenous hematin after liver transplantation for erythropoietic protoporphyria. *Transplantation.* 73:911-915; Rund, D., and Rachmilewitz, E. 2000. New trends in the treatment of beta-thalassemia. *Crit. Rev. Oncol. Hematol.* 33:105-118; Anderson, K. E., Bloomer, J. R., Bonkovsky, H. L., Kushner, J. P., Pierach, C. A., Pimstone, N. R., and Desnick, R. J. 2005. Recommendations for the diagnosis and treatment of the acute porphyrias. *Ann. Intern. Med.* 142:439-50. Hemin is also an established agent for HO-1 induction in several tested cultured cells and in vivo. Sato, H. et al., *FEBS Lett.* 405:219-223; Ishikawa, K., Sugawara, D., Wang, X., Suzuki, K., Itabe, H., Maruyama, Y., and Lusis, A. J.2001. Heme oxygenase-1 inhibits atherosclerotic lesion formation in ldl-receptor knockout mice. *Circ. Res.* 88:506-512; Kanakiriya, S. K., Croatt, A. J., Haggard, J. J., Ingelfinger, J. R., Tang, S. S., Alam, J., and Nath, K. A. 2003. Heme: a novel inducer of MCP-1 through HO-dependent and HO-independent mechanisms. *Am. J. Physiol. Renal Physiol.* 284:F546-554; Alam, J., Killeen, E., Gong, P., Naquin, R., Hu, B., Stewart, D., Ingelfinger, J. R., and Nath, K. A. 2003. Heme activates the heme oxygenase-1 gene in renal epithelial cells by stabilizing Nrf2. *Am. J. Physiol. Renal Physiol.* 284:F743-752; Graca-Souza, A. V., Arruda, M. A., de Freitas, M. S., Barja-Fidalgo, C., and Oliveira, P.L. 2002. Neutrophil activation by heme: implications for inflammatory processes. *Blood.* 99:4160-4165.

Conversion of trypsinogen to active trypsin within pancreatic acinar cells is an important event in developing acute pancreatitis. Furthermore, it has been well demonstrated that infiltrating neutrophils significantly contribute to this intrapancreatic trypsin activation. Gukovskaya, A. S., Vaquero, E., Zaninovic, V., Gorelick, F. S., Lusis, A. J., Brennan, M. L., Holland, S., and Pandol, S. J. 2002. Neutrophils and NADPH oxidase mediate intrapancreatic trypsin activation in murine experimental acute pancreatitis. *Gastroenterology.* 122:974-84. However, the mechanisms and signals that mediate neutrophil or other inflammatory cell (such as macrophage) recruitment into the pancreas are less well understood. Demonstrated herein is a novel protective role for hemin in experimental mouse pancreatitis and which provides a cellular mechanistic basis for such protection. This role is mediated by HO-1 and leads to recruitment of HO-1 expressing macrophages to the pancreas.

BRIEF DESCRIPTION OF THE INVENTION

In one aspect, the present invention provides a method of treating pancreatitis comprising administering to a human in need thereof an effective amount of hemin. The administration of hemin is preferably parenteral. As used herein, the term "parenteral" is given its ordinary and customary meaning in the field of pharmaceutical drug routes of administration. According to the Food and Drug Administration's Center for Drug Evaluation and Research Data Standards Manual (CDER Data Element Number C-DRG-00301; Data Element Name: Route of Administration) "parenteral" refers to administration by injection, infusion or implantation. Injection and infusion include administration into a vein (intravenous), into an artery (intraarterial), into a muscle (intramuscular), under the skin (subcutaneous), and into the peritoneum (intraperitoneal). Any appropriate route of administration set forth in the above-referenced Food and Drug Administration document is specifically included within the scope of the instant invention, and nothing herein shall be construed to limit in any way those routes of administration that would be useful in connection with administration of the hemin of the present invention.

In another aspect, the present invention provides a method of pancreatitis prophylaxis comprising administering to a human in need thereof an effective amount of hemin. As used herein, prophylaxis is given its ordinary and customary meaning in the medical art, generally defined as the prevention of or protective treatment for a disease, in this instance pancreatitis.

An effective amount of hemin is that amount that is determined to treat or be prophylactic for pancreatitis. An effective amount of hemin can be from 1 to 6 mg/kg/day, or more preferably from 1 to 4 mg/kg/day, although an effective amount of hemin can readily be determined by a treating or attending physician by considering, inter alia, the age of the patient, the extent of disease, and the overall medical condition of the patient. Accordingly, it is well within the ken of one of ordinary skill in the art to determine a pancreatitis prophylactic effective amount of hemin, or a pancreatitis treatment effective amount of hemin according to the teachings of the present invention.

In a still further aspect, the present invention contemplates a method of inducing an HO gene comprising administering to a human in need thereof an HO-inducing effective amount of hemin. An HO-inducing effective amount of hemin can be from 1 to 6 mg/kg/day or preferably 1 to 4 mg/kg/day, but as discussed elsewhere herein an HO-inducing effective amount can readily be determined by a worker of ordinary skill in the art based upon considerations of the human to be treated.

Preferably, the HO gene is the HO-1 gene. As used herein, induction or upregulation of an HO gene is given its ordinary and customary meaning, which includes turning on or turning up the expression of an HO gene by genetic mechanisms that are outside of the scope of the present invention. Those genetic mechanisms are not to be construed as limiting the invention to any particular theory of induction or upregulation of an HO gene. Induction or upregulation of an HO gene can be readily determined using methods and assays discussed elsewhere herein.

In a still further aspect, the present invention contemplates a method of inducing an HO gene in leukocytes for recruitment to the pancreas to treat pancreatitis comprising administering to a human in need thereof an HO-inducing effective amount of hemin. As used herein, the term leukocyte is given its ordinary and customary meaning, generally referring to any of several types of blood cells, including granulocytes (including neutrophils (heterophils), basophils and eosinophils; monocytes (including macrophages); and lymphocytes. The recruitment or migration to the pancreas of leukocytes in which an HO gene has been induced or upregulated is accomplished by mechanisms that are outside the scope of the present invention and should not be construed as limiting the invention to any particular mechanism or theory of recruitment or migration of leukocytes to the pancreas.

In another embodiment, the present invention contemplates a method of inducing an HO gene in leukocytes for recruitment to the pancreas for prophylaxis of pancreatitis comprising administering to a human in need thereof an HO-inducing effective amount of hemin.

In a yet further aspect, the present invention provides a method of ex vivo treatment of pancreatitis comprising a first step of providing peripheral blood leukocytes. Providing peripheral blood leukocytes ("PBLs") can be accomplished by techniques well known to those of ordinary skill in the art, including for example intravenous removal of leukocytes from the peripheral blood vasculature of a patient by venous puncture. PBLs are separated and isolated from other blood constituents by, for example by density gradient centrifugation with polysucrose followed by removal of the leukocyte layer.

The thus-obtained peripheral blood lymphocytes are next contacted with hemin to form induced peripheral blood lymphocytes. The PBLs are contacted with hemin by methods well known to those of ordinary skill in the art, including by admixing PBLs with hemin in vitro for a time and under conditions appropriate to induce the PBLs. More particularly, those genetic elements of the PBLs, such as the HO gene (and more preferably the HO-1 gene) are induced or upregulated, as discussed elsewhere herein.

Once the PBLs are induced with hemin, the PBLs are then infused into a human in need thereof. The induced PBLs are infused into a human in need thereof using techniques that are well known to those of ordinary skill in the art, including the parenteral administration of the induced PBLs into a human. Hemin or other agents can be pre-administered, or co-administered with the induced PBLs, to promote the selective migration of the induced PBLs to the pancreas. Humans in need of hemin-induced PBLs include humans that are suffering from pancreatitis, who are at risk for pancreatitis, or require prophylaxis against pancreatitis.

(A,B) Mice were injected intraperitoneally with hemin (H) or vehicle (V; 7 mice/group) every other day (3×; arrows) followed by injection with either saline (Sal) or caerulein (Cae) hourly (7×; arrows) and then harvesting of the pancreata and lungs at 12 h after first Sal or Cae injection. Sera were collected for amylase/lipase measurement. (C-E) Pancreatic and lung tissues (from panels A,B) were used to determine trypsin (pmol/mg protein) and myeloperoxidase (MPO; ng/mg wet tissue) enzyme activities and to assess extent of tissue injury. Data are presented as mean±SD. A representative hematoxylin and eosin staining of lung is shown (scale bar=50 μM). Note the marked hemorrhage and alveolar collapse in vehicle (a) compared to hemin (b) pretreated mice receiving caerulein.

FIG. 3: Hemin increases HO-1$^+$ pancreatic macrophages in association with MCP-1 and MIP-1α induction. (A) Pancreas from CDD-fed mice was triple-stained using antibodies to HO-1 (a), the macrophage marker F4/80 (b), and the granulocyte marker Gr-1 (c). Scale bar in panel d=20 μM. (B) Mice were treated intraperitoneally with hemin (H) or vehicle (V) once (H×1) or 3×(H×3, V×3) during a one week period, followed by feeding with CDD or regular chow for 3 d. Pancreata were collected followed by staining and counting F4/80$^+$ macrophages in 10 randomly selected high power fields (HPF). The mean±SD (3 mice/group) and p-value for the indicated comparisons are shown. (C) Hemin (H) or vehicle (V) were injected intraperitoneally once followed by harvesting of pancreata after 24 h. A non-injected control "C" group was also included. mRNA levels were then estimated from pancreata of 3 mice/group as a ratio of the indicated chemokine to β-actin (mean±SD). Changes in RANTES/ MIP-2 mRNA levels were not significant after V or H administration.

Figure 4:
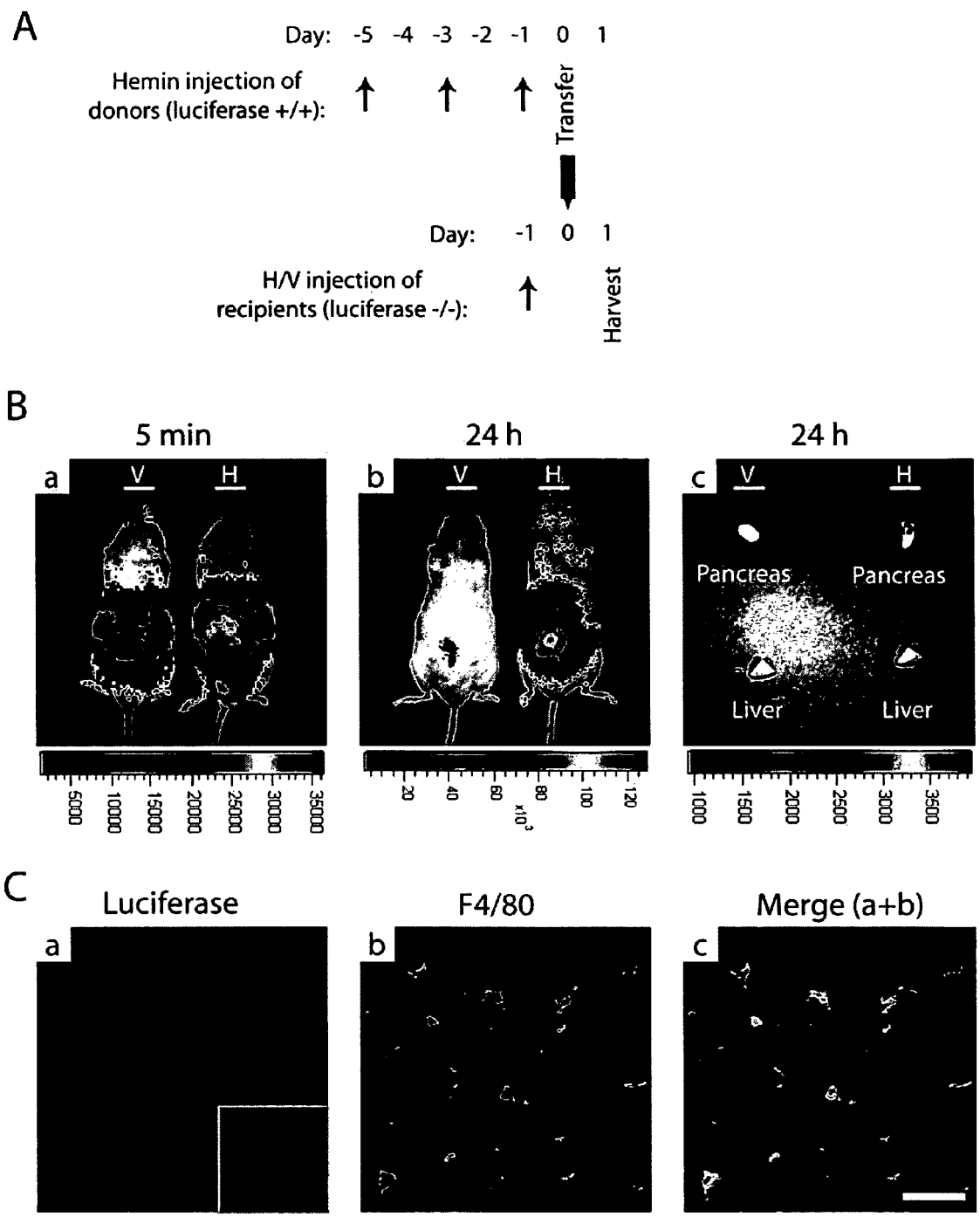

FIG. 4: Effect of hemin on in vivo macrophage homing to the pancreas using bioluminescence imaging. (A) Experimental scheme of cell transfer. Hemin (H) was injected 3× intraperitoneally into luciferase-overexpressing (+/+) mice, then peritoneal cells were harvested and macrophages were selected using anti-Mac-1 magnetic beads. Luciferase/Mac-1 double-positive cells were transferred intraperitoneally to wild-type (luciferase −/−) mice that were preinjected with one dose of H or vehicle (V) 24 h prior to the transfer. This hemin injection is necessary to induce pancreatic chemokines (FIG. 3C). (B) Live images of recipient intact anesthetized mice were taken 5 min (a) or 24 h (b) after cell transfer. Livers and pancreata were removed 24 h after the transfer followed by imaging (c). The signal intensity scale bar is shown below each image. (C) A duplicate of the pancreata shown in image c of panel B (from recipients receiving donor cells from H-injected animals) was double-stained with antibodies to luciferase and F4/80. Similar double-staining of pancreata from recipient animals receiving donor cells from V-injected mice showed background staining (e.g. insert of panel a for the anti-luciferase staining). Bar in panel c=50 μm.

FIG. 5: Protective effect of hemin-primed peritoneal cells on CDD-induced pancreatitis. (A) Peritoneal cells are isolated from hemin "H" or vehicle "V" pretreated mice (3 injections highlighted by arrows) then transferred intraperitoneally into naive recipient littermates followed by immediate initiation of CDD feeding. (B-D) After 2.5 d of CDD, sera were collected to measure amylase and BUN (mean ±SD, 6 mice/group). Pancreata were also collected for gross tissue assessment and for histological staining and scoring. Bar in panel D=50 μm, Vac=vacuoles, E=edema, Hem=hemorrhage, m1 and m2=pancreatic tissues from two separate mice per H/V group.

Figure 6:
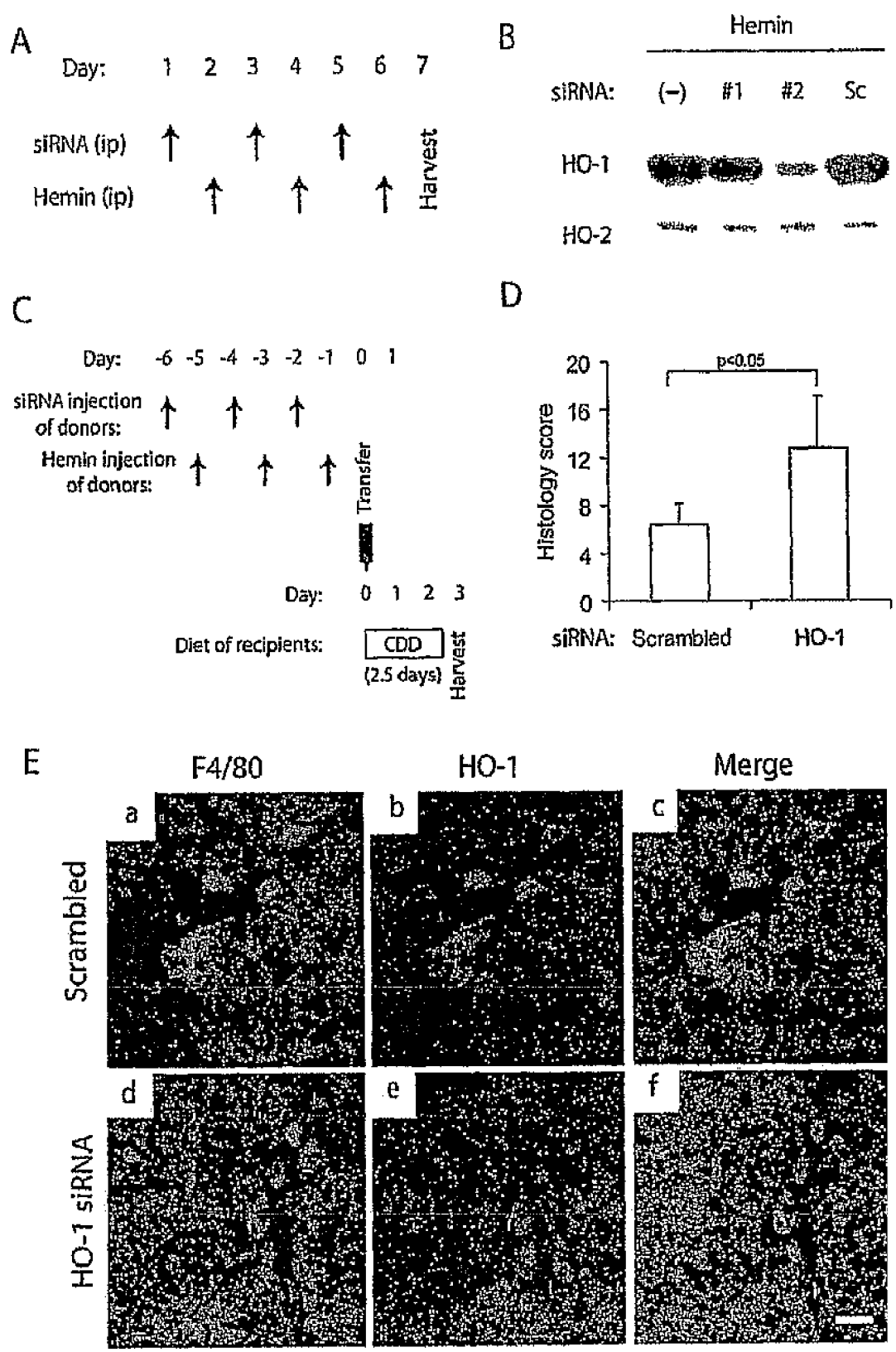

FIG. 6: Inhibition of the protective effect of hemin-primed peritoneal cells using HO-1 knock-down in vivo. (A,B) Peritoneal cells were isolated from hemin-treated mice that were also injected intraperitoneally on alternate days with saline (−), HO-1 siRNA (construct #1 and #2), or scramble control (Sc) siRNA. The peritoneal cells were then used to examine HO-1 and HO-2 levels by immunoblotting. (C,D) Peritoneal cells were harvested from hemin/construct #2 HO-1 siRNA or hemin/scrambled siRNA injected mice then transferred into naive recipient littermates followed by immediate initiation of CDD feeding. At 2.5 d of CDD feeding, pancreata were collected for histologic scoring. Data for histology score are presented as mean±SD (n=5-6/group), and are 6.4±1.7 (scrambled) and 12.7±4.5 (HO-1 siRNA). (E) Pancreata from panels C,D were double stained using antibodies to F4/80 and HO-1 (scale bar=20 μm).

Figure 7:
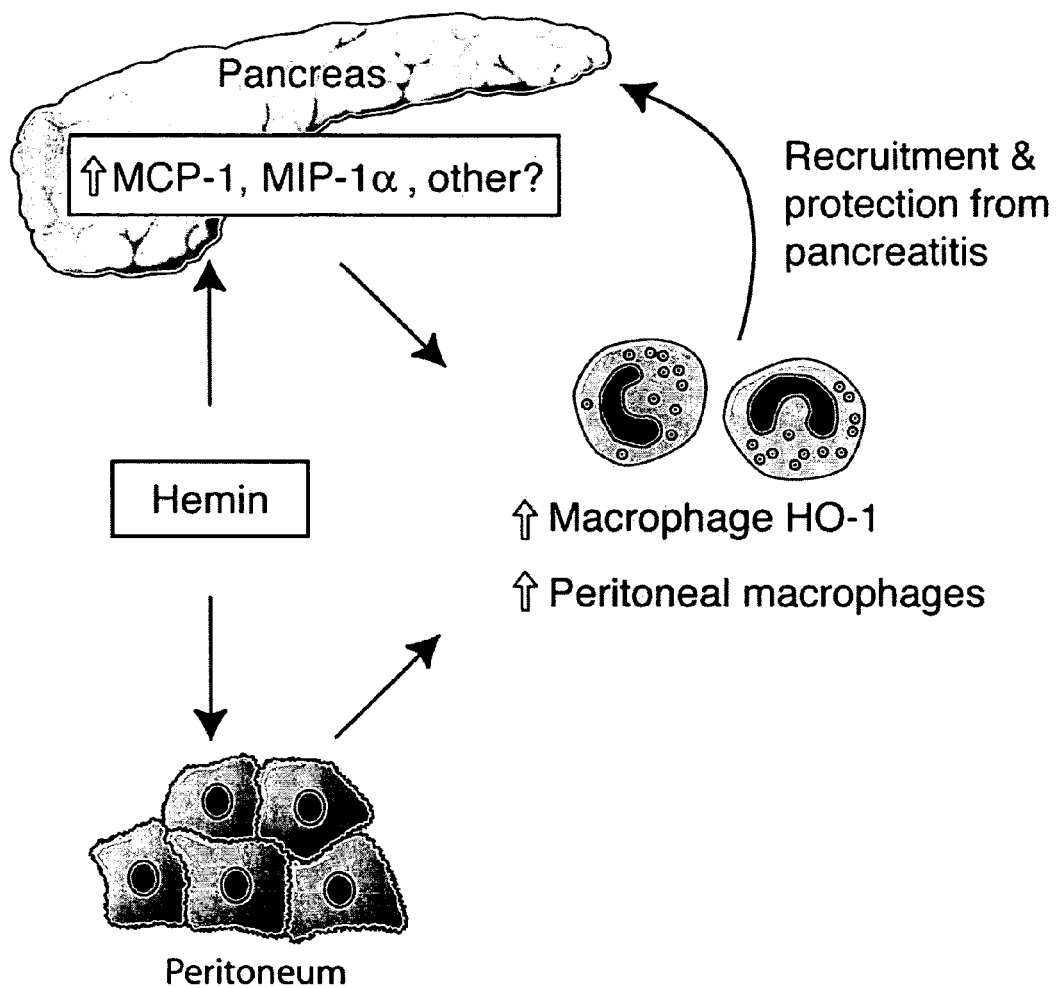

FIG. 7: Schematic of the effect of hemin on mouse HO-1 induction and homing of peritoneal macrophages to the pancreas. Hemin induces the expression of several pancreas chemokines and increases peritoneal macrophages and their HO-1 expression. Peritoneal macrophages that overexpress HO-1 home to the pancreas, and are able to provide significant protection from pancreatic injury.

Figure 8:
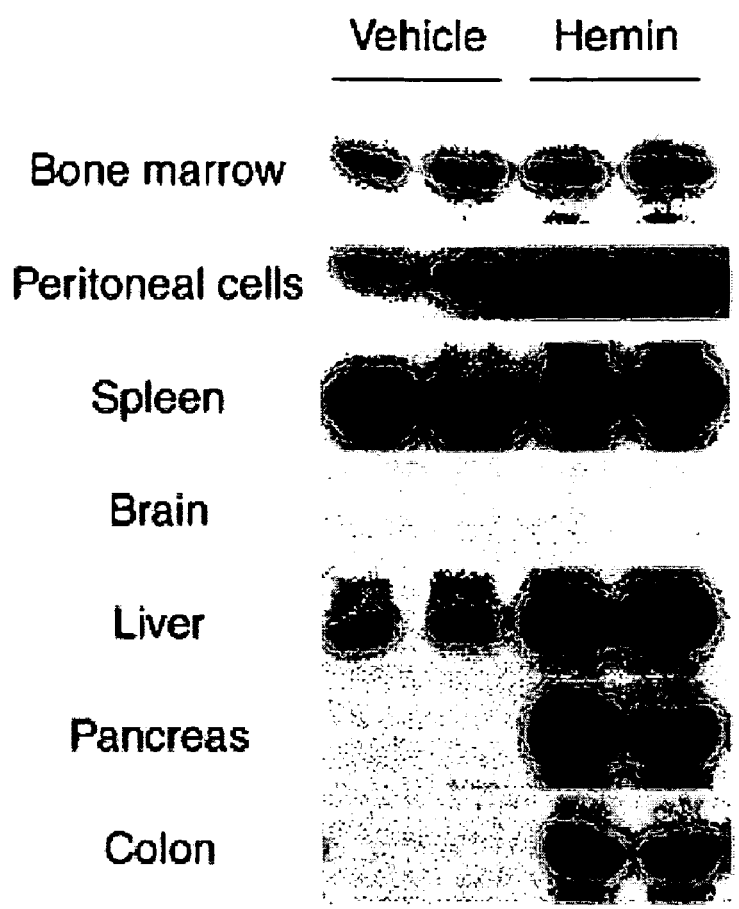

FIG. 8: HO-1 expression and hemin-mediated induction in mouse tissues and cells. Mice were injected 3× during 7d with vehicle or hemin (2 mice/group) followed by harvesting of the indicated organs and cells then preparation of total tissue/ cell homogenates. Protein concentrations of the homogenates were measured followed by SDS-PAGE separation (40 μg of protein/lane) then blotting using anti-HO-1 antibodies. Note the induction of HO-1 in peritoneal cells, liver, pancreas and colon (most prominent change being in pancreas) but not in bone marrow, spleen or brain. HO-2 levels did not change after hemin administration in any of the tissues (not shown).

Figure 9:
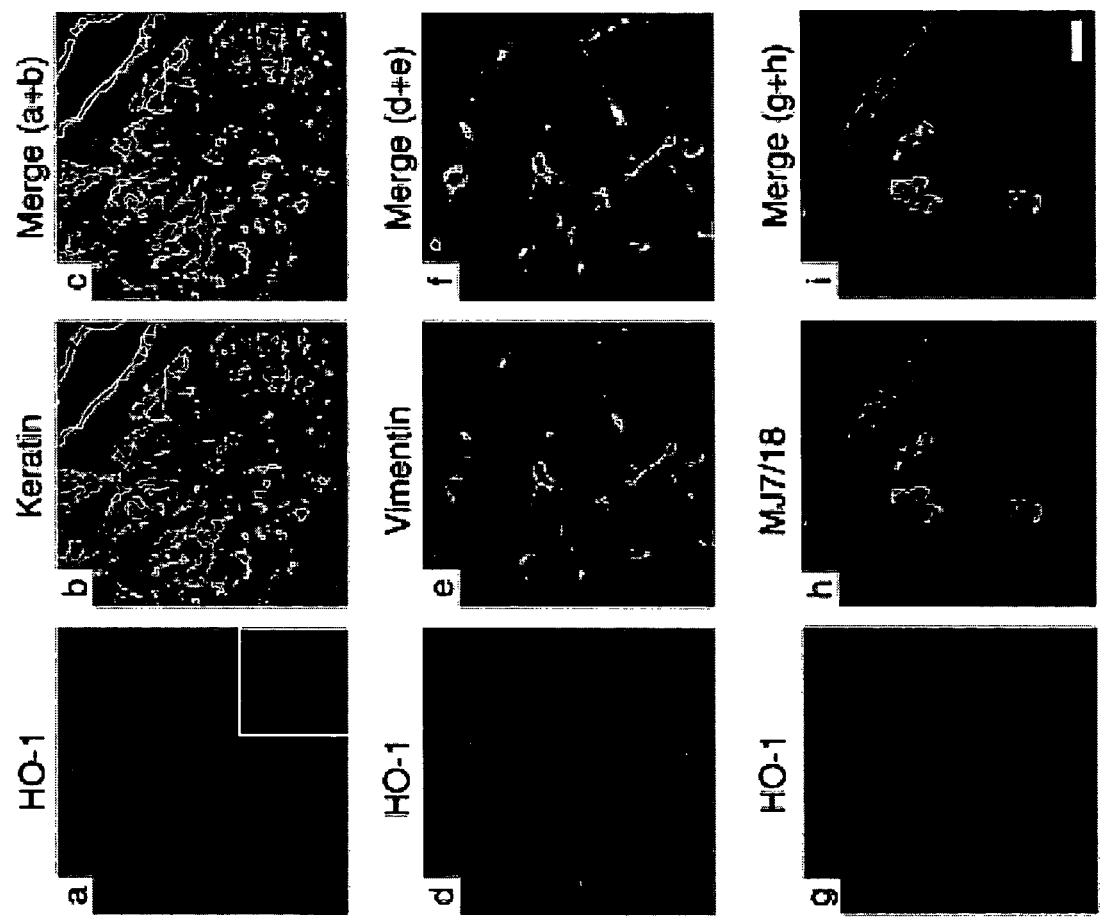

FIG. 9(*a*)-(*i*): Hemin induction of pancreatic HO-1 occurs in non-epithelial cells of mice fed CDD. Pancreata of mice pretreated with hemin followed by 3 days of CDD feeding were isolated, sectioned, then double-stained using antibodies to HO-1 (a, d and g) and keratin polypeptide 8 (epithelial marker, b), vimentin (mesenchymal marker, e) or MJ7/18 (endothelial marker, h). Merging of the indicated images is shown in the right panels. Scale bar in panel i=20 μm. HO-1 staining of pancreas from mice treated with vehicle alone (without CDD) afforded background staining (inset of panel a).

Figure 10:
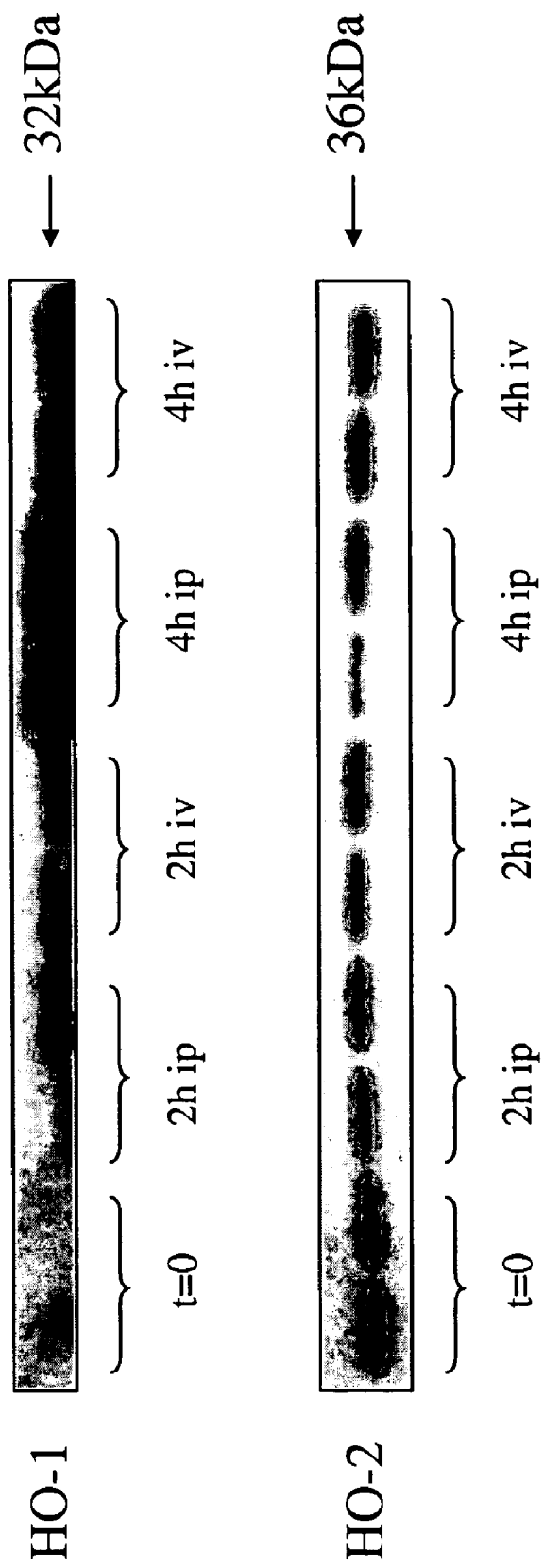

FIG. 10: Modes of panhematin (PH) administration as a potential therapeutic or prophylactic treatment modality in pancreatitis. Results from western blots of pancreatic lysate at t=0, 2 h, 4 h following single PH treatment given either intraperitoneally (ip) or intravenously (iv) is shown. Both ip and iv upregulate HO-1 rapidly whereas HO-2 remains unchanged.

Figure 11:
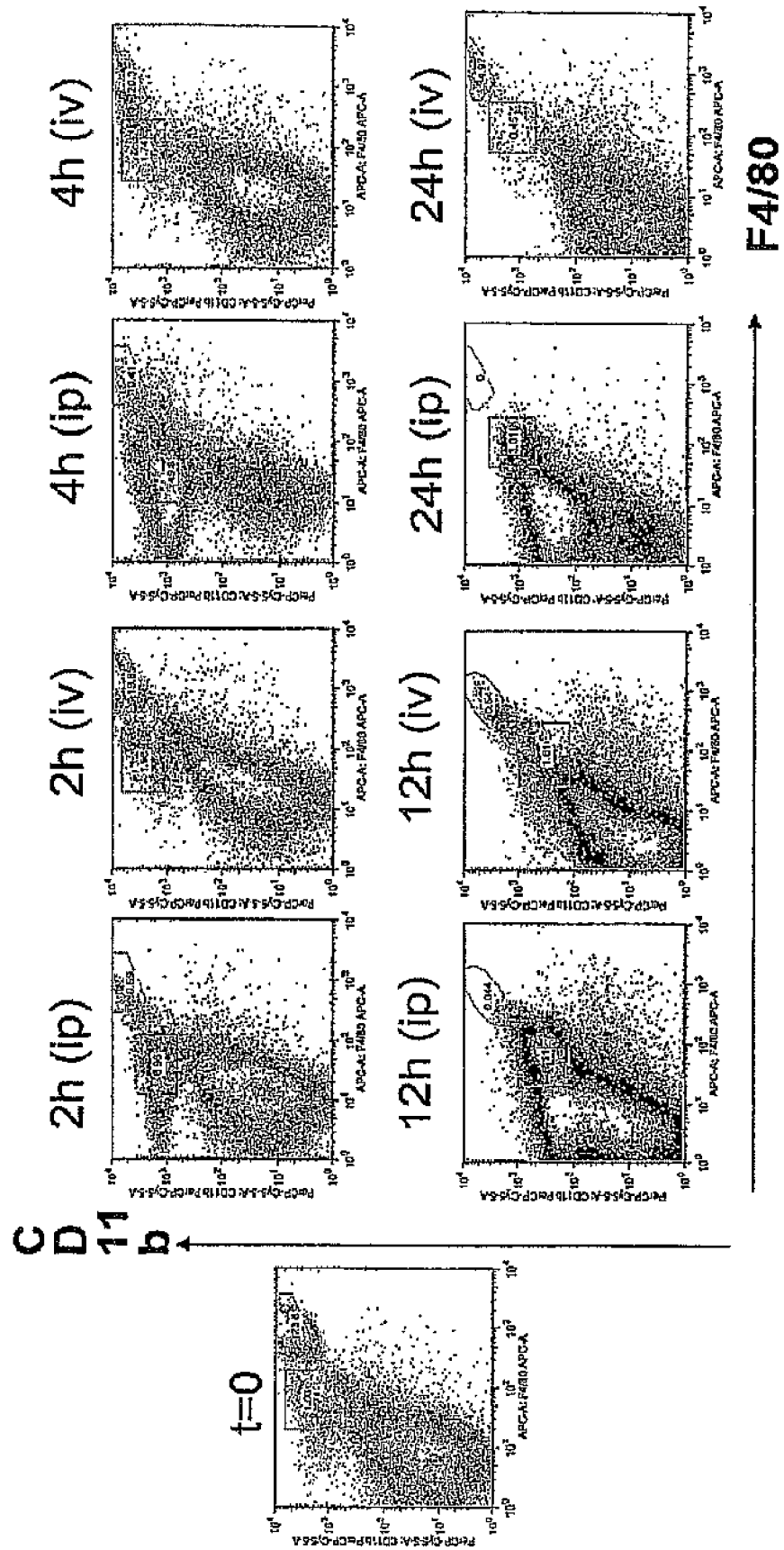

FIG. 11: Effect of PH injection on peritoneal cells over time. Flow cytometric analysis of peritoneal cells is shown following single PH injection given either iv or ip. Resident peritoneal macrophages (F4/80$^{hi}$CD11b$^{hi}$) are decreased following PH injection consistent with exit of these cells and appearance in the pancreas. This effect is delayed for the iv treated group as compared to ip group over time.

Figure 12:
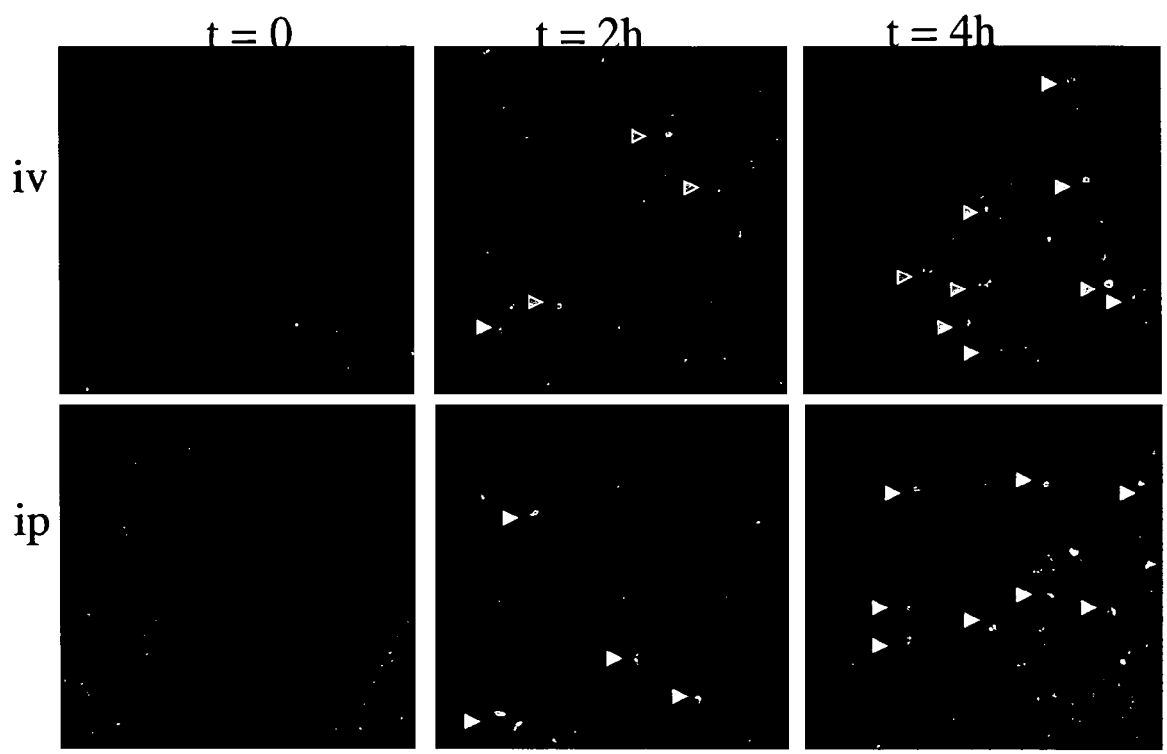

FIG. 12: Immunohistochemical stain of pancreas. Pancreata were isolated from mice treated with PH either ip or iv over time. Frozen sections were acetone fixed and stained with anti-HO-1 antibody. Consistent with the western blot findings, PH causes influx of HO-1$^+$ cells (highlighted by arrow heads in the right and middle panels) to the pancreas (magnification 20×).

DETAILED DESCRIPTION OF THE INVENTION

Figure 1:
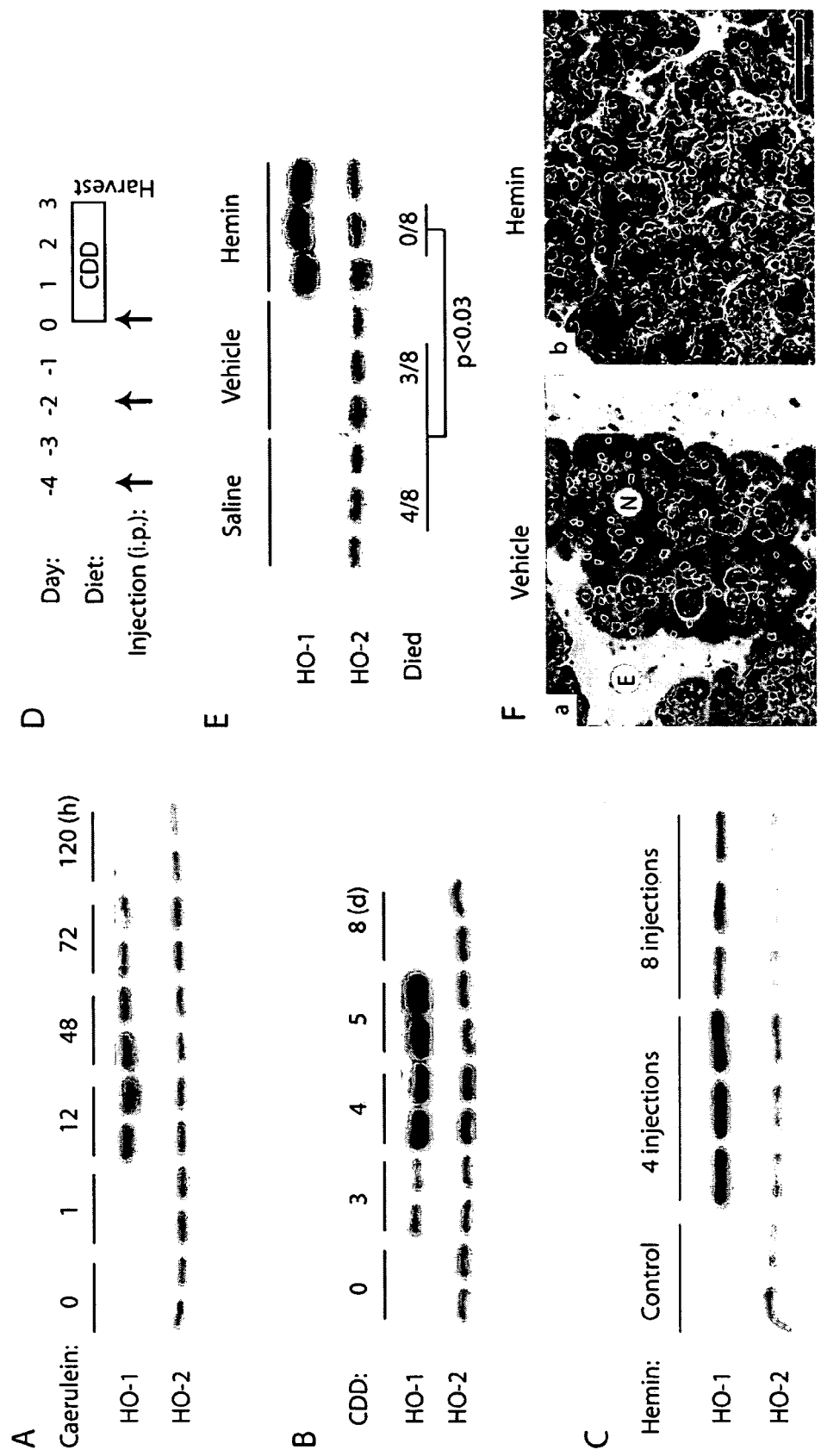
FIG. 1: Effect of hemin or pancreatic injury on HO-1 induction, and inhibition of pancreatic injury by hemin. (A, B) Total tissue homogenates were obtained from pancreata of caerulein-injected or choline deficient diet (CDD)-fed mice. Two age and sex-matched mice were used for each time point. Homogenates were tested by blotting using antibodies to HO-1 or HO-2. (C) Mice (3 mice/condition) were given hemin by intraperitoneal injection (4× during one week, or 8× during two weeks). Two "control" mice were injected with vehicle alone. Pancreatic homogenates were then obtained and blotted with anti-HO-1/2. (D-F) Mice were injected with saline, hemin, or vehicle (8 mice/group)3×(arrows) followed by feeding with CDD for 3 d then harvesting of the pancreata. HO-1 and HO-2 were analyzed by blotting of pancreatic homogenates (3 mice/group). The number of mice that died in each cohort of 8 mice is shown, and the survival difference was significant ($p<0.03$) when comparing controls (saline+ vehicle) versus hemin-injected mice. A representative hematoxylin and eosin staining of pancreata from mice that survived CDD feeding is shown (scale bar=50 μM). Note the marked pancreas edema (E) and necrosis (N) in the saline (not shown) and vehicle injected mice, as compared with the "hemin" group.
Figure 2:
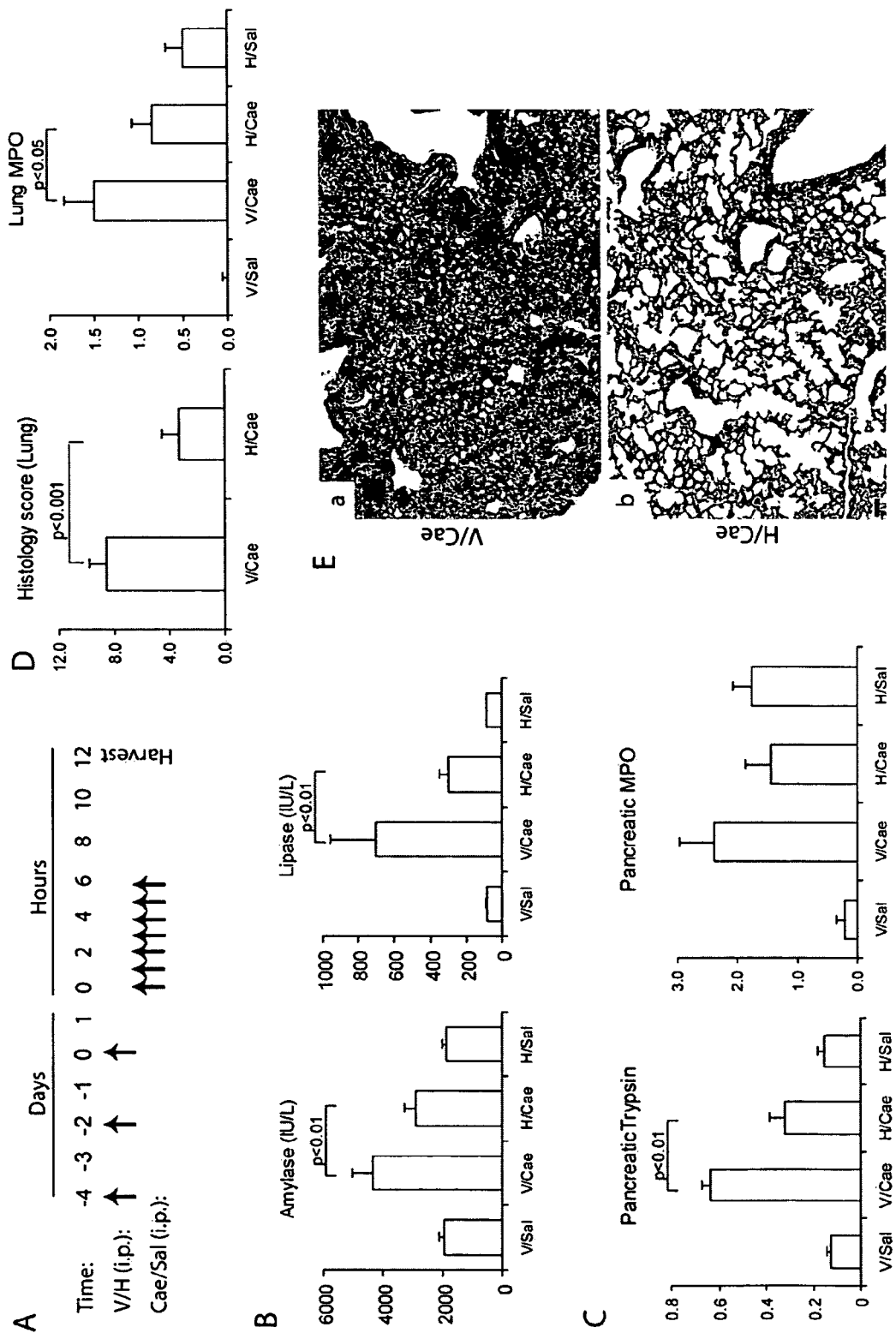
FIG. 2: Effect of hemin on caerulein-induced pancreatitis and its pulmonary complications.

The present invention offers a novel approach of immune-mediated therapy via the unanticipated effect of hemin on leukocyte recruitment to the pancreas. Based on a mouse animal model of pancreatitis, the therapeutic approach of the present invention has applicability to other mammalian, particularly human, pancreatitis. In the examples presented elsewhere herein, two types of cell transfers were performed. For both types of transfer experiments, the hemin-primed macrophages are derived from donor mice that were treated with three (3) doses of hemin (excessive dosing decreases the level of HO-1 induction, FIG. 1C). The difference between the bioluminescence transfer study (FIG. 4) and the other transfer experiments that involve CDD feeding (FIGS. 5, 6) is that in the latter CDD-related experiments hemin priming of the recipient mice is not required due to the effect of CDD on the pancreas which triggers homing of the transferred cells to the pancreas. In contrast, for the bioluminescence homing experiment (FIG. 4) a single dose of hemin priming is necessary since macrophages are not recruited to the pancreas unless the recipients receive the hemin priming which stimulates pancreatic chemokine production and triggers migration of macrophages to the pancreas (FIG. 3). Notably, intraperitoneal administration of panhematin [available from Ovation Pharmaceuticals, Inc., Deerfield, IL.] into mice also induces high pancreatic HO-1 levels. Although the relevant in vivo chemokines that are involved in macrophage recruitment to the pancreas remain to be defined, a cellular therapeutic approach can also be envisioned whereby autologous monocytes or other relevant cells can be activated by hematin ex vivo followed by re-infusion.

The demonstrated benefit of hemin or hemin-activated cell therapy in experimental mouse pancreatitis is prophylactic and is analogous to human use in high-risk patients undergoing endoscopic retrograde cholangiopancreatograms who can develop pancreatitis. Maschi, E., Mariani, A. Curioni, S., and Testoni, P.A. 2003. Risk factors for pancreatitis following endoscopic retrograde cholangiopancreatography: a meta-analysis. *Endoscopy.* 35:830-4. Therefore, hemin or hemin-based cell therapy can be considered as prophylaxis for potential iatrogenic pancreatitis caused by, for example, needed medical tests or interventions such as endoscopic retrograde cholangiopancreatography.

The present invention provides a method of treating pancreatitis by administering hemin to a patient in need thereof. In one embodiment, the hemin is delivered via a parenteral route. Preferably, the parenteral route is intraperitoneal. More preferably, the parenteral route is intravenous.

The effect of hemin or vehicle on peritoneal cell number was assayed. Mice (3 per group) were injected with vehicle or hemin during a 7-day period. Peritoneal cells were then isolated followed by counting. Cell viability was greater than 98% using trypan blue exclusion. The number of cells that were double positive for Mac-1$^+$ and F4/80$^+$ was then determined using flow cytometry. P-values compared the hemin treated versus the vehicle treated groups. The results are shown in the Table below.

|  | Vehicle Treated | Hemin Treated | p-Value |
| --- | --- | --- | --- |
| Total cell number | $3.1 \pm 1.0 \times 10^6$ | $7.3 \pm 2.1 \times 10^6$ | 0.06 |
| % Mac-1$^+$ and F4/SO$^+$ | 14.7 × 2.5% | 26.6 × 3.5% | 0.02 |

In another aspect, the present invention provides a method of preventing pancreatitis by administering hemin to a patient in need thereof. In one embodiment, the hemin is delivered via a parenteral route. In one embodiment, the parenteral route is intraperitoneal. In a preferred embodiment the parenteral route is intravenous.

The dosage of hemin depends upon various factors, including the age of the patient, the body weight of the patient, and the overall health of the patient, with particular focus on renal function or the presence of any coagulopathies or thrombocytopenia. Dosages of hemin useful in the present invention can range from about 1 to about 5 mg/kg/day, and more preferably from about 1 to about 4 mg/kg/day.

Hemin can be administered via a parenteral route, including intravenously or intraperitoneally. The choice of route of administration will depend upon factors considered by the attending physician, including accessibility of intravenous routes and need for rapid infusion of the hemin. Preferably, the route of administration is intravenously. Alternatively, the route of administration is intraperitoneal. Without wishing to be bound by theory, it is thought that intraperitoneal administration actively and effectively recruits intraperitoneal macrophages that travel to the pancreas to provide prophylaxis and treatment of pancreatitis.

The studies presented elsewhere herein indicate that CD11b/Mac-1 does not play a role in the migration of HO-1+ cells to the pancreas and the increased cells seen with the treatment may reflect the rise in circulating monocytes. In addition, CCR2 may be important for trafficking of "protective" monocyte/macrophage into pancreas since in its absence potential "pro-inflammatory" leukocyte may have advantage over the "protective" monocyte/macrophage to migrate into the pancreas and cause injury.

EXAMPLES

Materials and Methods

Hemin, vehicle and antibodies. Hemin (Sigma; St. Louis, Mo.) was dissolved in 10% ammonium hydroxide in 0.15 M NaCl to prepare a stock solution of 100 mg/ml, then further diluted 1:40 with sterile 0.15 M NaCl and injected into mice (10 μl/g). Vehicle injected mice received an identical NH$_4$OH-containing solution lacking hemin. The antibodies used were directed to: HO-1 and HO-2 (StressGen; Victoria, Canada); vimentin, smooth muscle actin, and luciferase (NeoMarkers; Fremont, Calif.); allophycocyanin-conjugated Gr-1 and Mac-1 (BD Pharmingen; San Diego, Calif.); and FITC-conjugated F4/80 (Serotec; Raleigh, N.C.). Panhematin was obtained from Ovation Pharmaceuticals, Inc. (Deerfield Ill.).

Mice and pancreatitis models. Experiments and animal care were performed according to approved institutional guidelines. Balb/c mice were housed under pathogen-free conditions and utilized in two established models of pancreatitis. Jensen, R. T., Lemp, G. F., and Gardner, J. D. 1980. Interaction of cholecystokinin with specific membrane receptors on pancreatic acinar cells. *Proc. Natl. Acad. Sci. U.S.A.* 77:2079-2083; Lombardi, B., Estes, L. W., and Longnecker, D. S. 1975. Acute hemorrhagic pancreatitis (massive necrosis) with fat necrosis induced in mice by DL-ethionine fed with a choline-deficient diet. *Am. J. Pathol.* 79:465-480; Algul, H., Tando, Y., Schneider, G., Weidenbach, H., Adler, G., and Schmid, R. M. 2002. Acute experimental pancreatitis and NF-kappaB/Rel activation. *Pancreatology.* 2:503-509; Toivola, D. M., Baribault, H., Magin, T., Michie, S. A., and Omary, M. B. 2000. Simple epithelial keratins are dispensable for cytoprotection in two pancreatitis models. *Am. J. Physiol. Gastrointest. Liver Physiol.* 279:G1343-1354; Zhong, B., Zhou, Q., Toivola, D. M., Tao, G. Z., Resurreccion, E. Z., and Omary, M. B. 2004. Organ-specific stress induces mouse pancreatic keratin overexpression in association with NF-kappaB activation. *J. Cell Sci.* 117:1709-1719. For caerulein-induced pancreatitis, age- and sex-matched mice were fasted for 12-16 h but allowed water ad libitum. Mice then received seven hourly intraperitoneal injections of saline (control group) or 50 μg/kg caerulein (Research Plus; Bayonne, N.J.) in saline, and were followed up to 12 h. For the pancreatitis induced by feeding a choline/methionine-deficient diet (CDD), young female mice (15-19 g) were fasted then fed CDD (Harlan Teklad; Madison Wis.) supplemented with 0.5% DL-ethionine (Sigma; St. Louis, Mo.) or normal chow (control group) for 3 d, then switched to normal diet for 1, 2 or 5 d.

Animal procedures. Mice were euthanized by CO$_2$ inhalation then pancreata and lungs were rapidly removed, divided into 3-4 pieces, and blood was collected by intracardiac puncture. Individual lung and pancreas fragments were immediately fixed in 10% formalin, embedded in OCT (Miles; Elkhart, Ind.) or snap-frozen in liquid N$_2$ for subsequent protein, enzyme, and RNA analysis. Toivola, D. M., et al., *Am. J. Physiol. Gastrointest. Liver Physiol.* 279:G1343-1354; Zhong, B., et al., *J. Cell Sci.* 117:1709-1719. Fixed tissues were sectioned then stained using hematoxylin and eosin (performed by Histo-tec Laboratory; Hayward, Calif.). Immunofluorescence staining was performed as described (29) and images were analyzed using confocal microscopy. Total tissue lysates were prepared by homogenization in Laemmli sample buffer and analyzed by SDS-PAGE followed by transfer to membranes for blotting and protein visualization by enhanced chemiluminescence. Trypsin activity was determined using a fluorimetric assay and the substrate Boc-Gln-Ala-Arg-MCA (Peptides International Inc.; Louisville, Ky.), and comparison to a standard curve generated with purified trypsin as described. Nathan, J. D., Romac, J., Peng, R. Y., Peyton, M., MacDonald, R. J., and Liddle, R. A. 2005. Transgenic expression of pancreatic secretory trypsin inhibitor-I ameliorates secretagogue-induced pancreatitis in mice. *Gastroenterology.* 128:717-27. For MPO activity, lung and pancreas tissues were processed as described [Oruc, N., Ozutemiz, A. O., Yukselen, V., Nart, D., Celik, H. A., Yuce, G., and Batur, Y. 2004. Infliximab: a new therapeutic agent in acute pancreatitis? *Pancreas.* 28:e1-8] followed by the use of an MPO kit according to manufacturer guidelines (Calbiochem; San Diego, Calif.). Lung injury after caerulein administration was assessed as previously described, based on neutrophilic infiltration, pulmonary edema, alveolar distension and collapse. Oruc, N., et al., *Pancreas.* 28:e1-8. P-values were calculated for histology, enzyme, and serum test comparisons using the paired t test; and for survival comparisons using the Chi-square method.

Real-time reverse transcription (RT)-PCR. Total RNA was isolated from pancreatic tissue using a commercial kit (TEL-TEST; Friendswood, Tex.). First strand cDNA was synthesized using oligo-dT primers and SuperScript II reverse transcriptase (Invitrogen; Carlsbad, Calif.). Real-time quantitative PCR was performed with an ABI Prism 7900 Sequence Detection System (PE Biosystems; Foster City, Calif.) and established primers for MCP-1, MIP-1α, MIP-2, RANTES, and β-actin. Zhong, B., et al., *J. Cell Sci.* 117: 1709-1719; Zhang, Y., McCormick, L. L., Desai, S. R., Wu, C., and Gilliam, A. C. 2002. Murine sclerodermatous graft-versus-host disease, a model for human scleroderma: cutaneous cytokines, chemokines, and immune cell activation. *J. Immunol.* 168:3088-3098; Walzog, B., Weinmann, P., Jeblonski, F., Scharffetter-Kochanek, K., Bommert, K., and Gaehtgens, P. 1999. A role for beta(2) integrins (CD11/CD18) in the regulation of cytokine20 gene expression of polymorphonuclear neutrophils during the inflammatory response. *FASEB J.* 13:1855-1865. Primers to β-actin were used as an internal control reference, and the amount of specific cytokine relative to actin transcript was determined and reported as mean±SD.

Luciferase transgenic mice and imaging. The luciferase-overexpressing transgenic mice (in an FVB/n background) and their nontransgenic counterparts [Cao, Y. A., Wagers, A. J., Beilhack, A., Dusich, J., Bachmann, M. H., Negrin, R.S., Weissman, I. L., and Contag, C. H. 2004. Shifting foci of hematopoiesis during reconstitution from single stem cells. *Proc. Natl. Acad. Sci. U.S.A.* 101:221-226] received 3 doses of hemin on days −5, −3, and −1. On day "0", peritoneal cells were harvested and the Mac-1$^+$ cells were selected using Mac-1 (anti-CD11b) coated microbeads (Miltenyi Biotec; Auburn, Calif.). Luciferase/Mac-1 double-positive cells (2×10$^6$) were transferred i.p. to wild-type FVB/n mice pretreated a day earlier with one dose of hemin or vehicle in order to prime cellular homing. Bioluminescent in vivo images of the recipient mice were obtained 5 min and 24 h after cell transfer as described. Cao, Y. A., et al., *Proc. Natl. Acad. Sci. U.S.A.* 101:221-226. Mice that were imaged 24 h after transfer were then killed followed by isolation of several organs for luciferase imaging and immunofluorescence staining.

Hemin pretreated peritoneal cell transfer into CDD-fed mice. Peritoneal cells were harvested from hemin or vehicle pretreated (3 doses given every other day) young female Balb/c mice (15-19 g). Isolated cells were washed with PBS, and equivalent cells were transferred into naive Balb/c littermates i.p. followed by initiation of CDD feeding. Mice were sacrificed after 2.5 d of CDD feeding, followed by isolation of the pancreata.(for histological and fluorescence staining) and blood. Serum was isolated from clotted blood followed by measurement of amylase and BUN using standard methods. The severity of pancreatitis was scored using established histological criteria that assigned individual numerical scores (1=mild, 2=moderate, 3=severe) to edema, inflammation, hemorrhage; and alternate scores for parenchymal necrosis (3=focal, 5=sublobular, and 7=lobular). Spormann, H., Sokolowski, A., and Letko, G. 1989. Effect of temporary ischemia upon development and histological patterns of acute pancreatitis in the rat. *Pathol. Res. Pract.* 184:507-513.

HO-1 siRNA and hemin pretreated cell transfer. Mice were injected i.p. every other day (3 total injections) with either saline or with two HO-1 siRNA constructs (2 mg/kg body weight), or with a scrambled siRNA sequence. Hemin was injected in the intervening days (an additional 3 injections). After 7 days, peritoneal cells were harvested and analyzed by immunoblotting using antibodies to HO-1/2. Since significant inhibition of HO-1 occurred with construct #2, construct #2 was used for subsequent transfer of peritoneal cells (pretreated with hemin+scrambled siRNA or with hemin+HO-1 siRNA) to naive recipient mice that were then fed CDD for 2.5 days followed by isolation of the pancreata. The siRNAs were synthesized by Dharmacon Research Inc. (Lafayette, Colo.) and tested previously. Zhang, X., Shan, P., Jiang, D., Noble, P. W., Abraham, N. G., Kappas, A., and Lee, P. J. 2004. Small interfering RNA targeting heme oxygenase-1 enhances ischemia-reperfusion-induced lung apoptosis. *J. Biol. Chem.* 279:10677-10684. The sense and antisense strands sequences of the two HO-1 siRNA and nonspecific siRNA scrambled duplex were:

[SEQ ID NO. 1]
(#1) 5'-UGGCUUCCUUGUACCAUAUdTdT-3' (sense)
and

[SEQ ID NO. 2]
5'-AUAUGGUACAAGGAAGCCAdTdT-3' (antisense);

[SEQ ID NO. 3]
(#2) 5'-GCCACACAGCACUAUGUAAdTdT-3' (sense)
and

[SEQ ID NO. 4]
-continued
5'-UUACAUAGUGCUGUGUGGCdTdT-3' (antisense);
and

[SEQ ID NO. 5]
(scrambled) 5'-GCGCGCUUUGUAGGAUUCGdTdT-3' (sense)
and

[SEQ ID NO. 6]
5'-CGAAUCCUACAAAGCGCGCdTdT-3' (antisense).

Un-treated mice were compared with groups treated with panhematin via an intravenous or intraperitoneal route. Mice were also treated with anti-Mac-1 antibody either at the time of or 1 h prior to treating with intraperitoneal panhematin. In addition, wild-type or CCR2-/- mice were treated with either panhematin or vehicle. Western blot analysis and immunohistochemistry (IHC) were used to determine HO-1 expression in the pancreas. Flow cytometric analysis (FACS) was used to phenotype peritoneal and blood leukocytes.

Both intravenous and intraperitoneal administration of panhematin induce HO-1 expression in the pancreas as early as 2 hours after administration. Using FACS analysis, resident peritoneal macrophages (F4/80hiCD11bhi) were decreased at 4 hours in the intraperitoneal group and were no longer present by 12 hours. Similarly by IHC, HO-1+ cells were identified in the pancreas in both intravenous and intraperitoneal treated groups as early as 4 hours and increased in numbers by 24 hours. When mice were treated with anti-Mac-1 antibody at the time of panhematin administration (and especially given 1 h prior), increased numbers of HO-1+ cells were observed in the pancreas 4 hours later by IHC. Furthermore, treatment with anti-Mac-1 antibody caused an accumulation of monocytes in the circulation and did not prevent the disappearance of peritoneal resident macrophages. Surprisingly panhematin treatment alone caused pancreatitis in CCR2-/- mice. Panhematin injected either intravenously or intraperitoneally induces HO-1 within 2 hours and causes migration of HO-1+ cells into the pancreas.

We claim:

1. A method of treating pancreatitis comprising administering to a human in need thereof an effective amount of hemin.

2. A method of pancreatitis prophylaxis comprising administering to a human in need thereof an effective amount of hemin.

3. The method of claims 1 or 2 wherein said hemin is administered via a parenteral route.

4. The method of claim 3 wherein said pareneteral route is intravenous.

5. The method of claim 3 wherein said parenteral route is intraperitoneal.

* * * * *